(12) United States Patent
Kyriakou

(10) Patent No.: US 9,968,324 B2
(45) Date of Patent: May 15, 2018

(54) GENERATING A 2D PROJECTION IMAGE OF A VASCULAR SYSTEM

(71) Applicant: Yiannis Kyriakou, Spardorf (DE)

(72) Inventor: Yiannis Kyriakou, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 37 days.

(21) Appl. No.: 14/597,894

(22) Filed: Jan. 15, 2015

(65) Prior Publication Data
US 2015/0201897 A1 Jul. 23, 2015

(30) Foreign Application Priority Data

Jan. 22, 2014 (DE) .................. 10 2014 201 134

(51) Int. Cl.
*A61B 6/00* (2006.01)
*A61B 5/026* (2006.01)
(Continued)

(52) U.S. Cl.
CPC .......... *A61B 6/5223* (2013.01); *A61B 5/0263* (2013.01); *A61B 5/489* (2013.01);
(Continued)

(58) Field of Classification Search
None
See application file for complete search history.

(56) References Cited

U.S. PATENT DOCUMENTS

| 7,024,027 B1 | 4/2006 | Suri et al. |
| 2005/0215881 A1 | 9/2005 | Van Zijl et al. |

(Continued)

FOREIGN PATENT DOCUMENTS

| CN | 1685243 A | 10/2005 |
| CN | 101115989 A | 1/2008 |

(Continued)

OTHER PUBLICATIONS

Chinese Office Action for related Chinese Application No. 2015 100 171 43.8 dated Jan. 25, 2017, with English Translation.
(Continued)

*Primary Examiner* — Tse Chen
*Assistant Examiner* — Patrick M Mehl
(74) *Attorney, Agent, or Firm* — Lempia Summerfield Katz LLC

(57) ABSTRACT

The embodiments relate to generating a 2D projection image of a vascular system of a body region of interest, including: (1) acquiring a 3D dataset of the body region of interest, (2) acquiring at least one 2D projection image of the body region of interest (S3), (3) generating a modified 3D dataset by eliminating vessels whose size exceeds a predetermined limit value, (4) normalizing the 2D projection image using projection data of the modified 3D dataset, (5) eliminating vessel projections in the normalized 2D projection image whose size exceeds a predetermined limit value, (6) interpolating the areas of the 2D projection image in which the vessel projections have been eliminated, and (7) denormalizing the normalized and interpolated 2D projection image using projection data of the modified 3D dataset.

16 Claims, 2 Drawing Sheets

(51) Int. Cl.
    *A61B 5/00*     (2006.01)
    *A61B 6/03*     (2006.01)
(52) U.S. Cl.
    CPC .......... *A61B 5/7425* (2013.01); *A61B 5/7445* (2013.01); *A61B 6/032* (2013.01); *A61B 6/4441* (2013.01); *A61B 6/462* (2013.01); *A61B 6/463* (2013.01); *A61B 6/504* (2013.01); *A61B 6/5205* (2013.01); *A61B 2576/02* (2013.01)

(56) References Cited

U.S. PATENT DOCUMENTS

| | | | |
|---|---|---|---|
| 2007/0116332 A1* | 5/2007 | Cai | G06K 9/4609 382/128 |
| 2008/0101667 A1 | 5/2008 | Begelman et al. | |
| 2008/0192887 A1* | 8/2008 | Weese | A61B 6/481 378/41 |
| 2011/0007956 A1* | 1/2011 | Meyer | A61B 6/032 382/131 |
| 2011/0249877 A1 | 10/2011 | Begelman et al. | |
| 2014/0003688 A1 | 1/2014 | Hansis | |

FOREIGN PATENT DOCUMENTS

| | | |
|---|---|---|
| CN | 101900823 A | 12/2010 |
| CN | 103310432 A | 9/2013 |
| DE | 102009032059 A1 | 1/2011 |
| DE | 102011005634 A1 | 9/2012 |
| WO | WO03042921 A1 | 5/2003 |

OTHER PUBLICATIONS

Chinese Search Report for Chinese Application No. 201510017143.8, dated Aug. 11, 2017, with English Translation.
German Office Action dated Oct. 15, 2014 for corresponding German Patent Application No. DE 10 2014 201 134.5 with English translation.
"Syngo iFlow/Dynamic Flow Evaluation/Answers for life," Siemens AG, Medical Solutions, Angiography, Fluoroscopic and Radiographic Systems, pp. 1-24, 2008.

* cited by examiner

GENERATING A 2D PROJECTION IMAGE OF A VASCULAR SYSTEM

CROSS-REFERENCE TO RELATED APPLICATIONS

This application claims the benefit of DE 10 2014 201 134.5, filed on Jan. 22, 2014, which is hereby incorporated by reference in its entirety.

TECHNICAL FIELD

The embodiments relate to a method and a device for generating at least one 2D projection image of a vascular system of a body region of interest, in particular of the parenchyma, in particular of the human or animal body.

BACKGROUND

Different technologies are known for visualizing a vascular system of the human or animal body. In a form of digital subtraction angiography (DSA), after administration of a contrast agent two-dimensional projection images are acquired repeatedly at a predetermined, fixed projection angle by an X-ray apparatus, a reference image (e.g., mask image) is subtracted from each image. During the procedure, the mask image is generated at a point in time at which no contrast agent is present. In this way, the arrival of the contrast agent in the vessels, and so the blood flow, may be visualized (e.g., perfusion). Owing to the subtraction of the individual time-series images from the mask image, the visualizations from now on contain only the vessels filled with contrast agent. The background (e.g., tissue, bone, air) is suppressed. Digital subtraction angiography plays a major role in diagnostics, for example, in the detection of pathological vascular diseases in the brain.

A tool by the name of Syngo iFlow is known that generates a parametric visualization of the arrival time of a contrast agent bolus based on digital subtraction angiography. The individual images of the DSA series (e.g., time-series images) are combined into a parametric image in which the arrival time of the contrast agent bolus may be visualized in color-coded form. In this case, the arrival time is, for example, the time up until the contrast agent reaches its maximum intensity; a so-called time-to-peak map (TTP map) is produced. An early arrival time of the contrast agent may be represented, for example, in a color from the red color spectrum, and a late arrival time in a color from the green or blue color spectrum. More information on this may be found in the publication titled "syngo iFlow/Dynamic Flow Evaluation/Answers for life" published by Siemens AG, Medical Solutions, Angiography, Fluoroscopic and Radiographic Systems.

In many cases, only the (e.g., smaller) vessels of the parenchyma (e.g., tissue) are of interest in the angiographic images, in digital subtraction angiography, for example, although the vessels are often obscured to a great degree by the large affarent and/or efferent vessels (e.g., arteries, veins). Currently, however, it is not possible to eliminate the large vessels from the projection images obtained by digital subtraction angiography.

In addition to conventional two-dimensional subtraction angiography, imaging techniques are known that enable a three-dimensional visualization of a vascular system or of the blood flow, referred to as 3D angiography or 3D perfusion. Computed tomography (CT angiography, perfusion CT), magnetic resonance tomography (magnetic resonance angiography, magnetic resonance perfusion imaging) as well as C-arm-based imaging may be cited here by way of example. Basically, these three-dimensional techniques may also apply the subtraction principle, thus enabling pure vessel visualizations to be generated while suppressing the background. With the three-dimensional techniques, it is known to segment large vessels, (e.g., to classify them as such and where necessary to remove them from the visualization). The use of three-dimensional techniques during a treatment, however, is subject to restrictions and the temporal resolution is poorer than in the case of the 2D techniques.

SUMMARY AND DESCRIPTION

The scope of the present invention is defined solely by the appended claims and is not affected to any degree by the statements within this summary. The present embodiments may obviate one or more of the drawbacks or limitations in the related art.

The object underlying the embodiments is to disclose a method and a device that enable smaller vessels, (e.g., vessels of the parenchyma), to be visualized in the most clearly discernible manner possible in a 2D projection image, (e.g., obtained by two-dimensional dynamic subtraction angiography).

The method includes: (1) acquiring a 3D dataset of the body region of interest, (2) acquiring at least one 2D projection image of the body region of interest, (3) generating a modified 3D dataset by eliminating vessels whose size exceeds a predetermined limit value, (4) normalizing the 2D projection image using projection data of the modified 3D dataset, (5) eliminating vessel projections in the normalized 2D projection image whose size exceeds a predetermined limit value, (6) interpolating the areas of the 2D projection image in which the vessel projections have been eliminated, and (7) denormalizing the normalized and interpolated 2D projection image using projection data of the modified 3D dataset.

The computer program product has a computer-readable data medium and a program code of a computer program. The program code is stored on the data medium and is configured to control the method when the computer program is executed on a computer.

The control and computing unit has a program memory for storing a program code, the program code being configured to control the method.

The device has a first acquisition apparatus for acquiring a 3D dataset of the body region of interest, a second acquisition apparatus for acquiring at least one 2D projection image of the body region of interest, and a control and computing unit that is configured to control the method. The first and second acquisition apparatus may be embodied as separate acquisition apparatuses or as a common or the same acquisition apparatus.

The method and the device enable large vessels (e.g., vessels having a predetermined minimum size) to be eliminated in a 2D projection image in order to generate a visualization of the (e.g., smaller) vessels of the parenchyma, referred to as a virtual parenchymogram.

For this purpose a 3D dataset of the body region of interest is acquired in the first instance, which operation may be carried out independently in time of the acquisition of the 2D projection image. The 3D dataset may be an angiographic image that, in particular, represents the blood volume (e.g., parenchymal blood volume (PBV)). The acquisition of the 3D dataset includes, e.g., the acquisition of two-dimensional X-ray projection images from different projection directions and the reconstruction of a three-dimensional image dataset from the two-dimensional projection images, for example, by a back projection method or some other reconstruction method. These techniques are generally known in the prior art and therefore will not be described in any further detail at this point.

During, prior to, or after the acquisition of the 3D dataset, a projection image of the same body region is generated, for example, by an X-ray acquisition.

The 3D dataset contains the vessels of the imaged body region as well as, where applicable, background, such as bone, tissue and/or air, for example. In particular, the 3D dataset contains the vessel geometry, (e.g., information relating to the three-dimensional structure of the vessels and the position of the vessels in space). The 3D dataset therefore contains a three-dimensional map of the vessels of the body region of interest. The body region may be in a "steady state" such that all the vessels are uniformly contrasted, e.g., because they are filled with contrast agent (e.g., static visualization).

In one embodiment, the vessels in the 3D dataset are segmented, with the result that the 3D dataset exclusively contains the vessel information (e.g., without background).

The 2D projection image contains a projection visualization of the vessels of the body region of interest and, in principle, may be generated from an arbitrary projection direction. In particular, the 2D projection image contains not only the parenchymal vessels, in other words, the vessels of the tissue, but also the large afferent and efferent vessels.

Certain vessels whose size exceeds a predetermined limit value are segmented out of the 3D dataset, which initially also contains all of the vessels, e.g., both the parenchymal vessels and the afferent and efferent vessels (e.g., arteries, veins). In this way, a modified 3D dataset may be generated that no longer contains the afferent and efferent vessels, e.g., from this point on includes only the vessels of the so-called microcirculation. The modified 3D dataset may also be referred to as a three-dimensional dataset of the parenchymal blood volume (PBV). The 3D dataset may, if desired, be visualized by a display apparatus and also be referred to as a 3D acquisition, in particular, a 3D PBV acquisition. The modified 3D dataset therefore now contains only the section of the vascular system that is of interest, in particular without the large afferent and efferent vessels (e.g., arteries, veins).

Projection data may be generated from the modified 3D dataset in a generally known manner by a forward projection. The projection data is used for normalizing the 2D projection image, (e.g., the 2D projection image is normalized using projection data obtained from the modified 3D dataset). For this purpose, the forward projection is performed along the same projection direction as that of the 2D projection image. The projection data of the 3D dataset obtained in this way forms a projection image that, in contrast to the 2D projection image, from now on contains only the regions of interest of the vascular system. By normalization in the present context is to be understood in particular a division of the 2D projection image by the projection image (e.g., projection data) computed from the modified 3D dataset.

In the normalized 2D projection image, those vessel projections whose size exceeds a predetermined limit value are segmented out and the corresponding areas are filled with artificial data, e.g., by non-linear interpolation. In this case, the non-linear interpolation produces a soft image impression and eliminates the large vessels. All other information, however, in the areas is also lost.

In order to reinstate certain parenchymal information or, as the case may be, information relating to the vessels of the parenchyma, the interpolated projection data (2D projection image) is denormalized, specifically on the basis of the modified 3D dataset, which exclusively contains the parenchymal volume, e.g., the filling of the parenchyma. Toward that end, analogously to the preceding normalization, line integrals are calculated through the 3D dataset (e.g., containing the vessels of the parenchyma) and used to denormalize the interpolated 2D projection image. In this way, anatomical information is incorporated back into the 2D projection image. Denormalization in the present context is to be understood in particular a multiplication of the 2D projection image by the projection image (e.g., projection data) computed from the modified 3D dataset.

In one embodiment, the vessels of the 3D dataset whose size exceeds a predetermined limit value are projected into the, in particular normalized, 2D projection image and that the elimination of those vessel projections in the normalized 2D projection image whose size exceeds a predetermined limit value is carried out on the basis of the projected vessels of the 3D dataset. The segmented vessels from the 3D PBV acquisition are projected into the 2D projection image (the 2D iFlow projection, for example) and their two-dimensional "tracks" marked. The large vessels are identified in the 2D projection image on the basis of the marking. The large vessels are therefore segmented out in the 3D dataset. The segmented large vessels are projected into the 2D projection image in order to identify the corresponding large vessels there. In this way, the large vessels may be recognized in the 2D projection image. Because of the spatial information present, the segmentation of the large vessels is easier and more accurate in the 3D dataset than in the 2D projection image.

In another embodiment, the 3D dataset is generated by computed tomography (CT), magnetic resonance tomography (MRT) or C-arm-based imaging. Examples of a computed tomography modality are DynaCT PBV or multi-slice computed tomography (MSCT). Magnetic resonance tomography may be in particular an MR perfusion scan. In magnetic resonance angiography, an atlas-based segmentation and classification may be carried out in order to compute attenuation maps from the MR data. The 3D dataset (PBV acquisition) may be produced on the basis of a subtraction so that only the fill volume (without environment, for example bone) is included. The 3D dataset may be a static visualization of the vessels in which all of the vessels are filled (without time information).

The 2D projection image may be generated by the digital subtraction angiography (DSA) method. With this approach, a differential image is generated between a fill image acquired while a contrast agent is administered and a mask image free of contrast agent. The difference is calculated one pixel at a time. As a result of the DSA, there remains as the final image an acquired image depicting only the contrast-agent-filled vascular system (e.g., without tissue, bone, etc.).

In a particular embodiment, a time series of 2D projection images (DSA series) is acquired. The contrast-agent-free mask image is subtracted from each projection image of the time series so that the uptake of the contrast agent may be visualized. This technique is generally known and will not be described in any further detail here. The generation of the DSA series may also be referred to as dynamic two-dimensional DSA.

A particularly illustrative visualization of the perfusion may be achieved by generating or calculating, from the time series of 2D projection images (DSA series), a final or cumulative 2D projection image that contains information about the inflow of contrast agent into the vascular system, in particular the parenchyma. With this approach, the individual images of the DSA series (e.g., time-series images) are assembled into a parametric overall image in which specific contrast agent inflow parameters are included, e.g., the time of maximum contrast agent concentration (e.g., time-to-peak), the inflow time instant, the blood flow or the blood volume (e.g., time-to-peak map, 2D parametric DSA visualization). The 2D projection image may be a parametric visualization of the inflow of contrast agent into the vascular system, in particular, in the form of a time-to-peak map.

In a further embodiment, an associated modified 3D dataset is generated for each image of the DSA series, those regions of the vascular system that are not filled in the respective 2D projection image being eliminated in the 3D dataset, and that the normalization and/or denormalization are/is performed for each image of the DSA series on the basis of the respective associated modified 3D dataset. The background hereto is that in an embodiment, the PBV map (e.g., 3D dataset without the large vessels) represents only one point in time at which the vascular system is completely filled. It is therefore provided at the time of segmentation or forward projection to synchronize which vessel region is filled in the 2D series at the respective point in time. A synchronization in respect of which regions of the vascular system are filled therefore takes place for each image of the 2D series. Those regions that are not filled in the 2D projection image at the respective point in time are eliminated in the 3D dataset. This may take place based on a back projection of the 2D image onto the 3D dataset. By a binary analysis (e.g., voxel filled yes/no?), a modified 3D dataset is generated for each time-series image of the DSA series, in which modified 3D dataset the unfilled voxels in each case have been removed. This act may be performed prior to the normalization and/or denormalization. Furthermore, this act may be performed before the large vessels are segmented out.

The 3D dataset may be acquired likewise on the basis of a subtraction. In this case a three-dimensional mask image dataset is subtracted from a three-dimensional contrast agent dataset (e.g., voxel-by-voxel subtraction) such that only the signals due to the contrast agent remain. The corresponding method may be described as three-dimensional subtraction angiography. After the large vessels (e.g., arteries, veins) have been segmented out, only the vessels of the parenchyma still remain. The remaining differential image dataset may in this case be referred to as the parenchymal blood volume (PBV). An embodiment therefore may be seen in using a dataset of the parenchymal blood volume (PBV dataset) obtained on the basis of subtraction angiography in order to normalize and/or denormalize the 2D projection image.

The normalization and/or denormalization may be performed one picture element at a time (e.g., pixel by pixel). In the normalization, the picture elements of the 2D projection image are divided by the corresponding pixels of the forward projection of the 3D dataset. In the denormalization, the picture elements of the 2D dataset are multiplied by the corresponding pixels of the forward projection of the 3D dataset. By this denormalization, in particular in the areas containing the interpolated data, anatomical information from the 3D dataset is incorporated into the 2D projection image.

The advantages and effects described in connection with the method are achieved by the computer program product, the control and computing unit, and the device. In this respect reference is made to the above statements.

The device is configured in particular to perform the method. In this regard the provided acquisition apparatuses may also be realized by a single acquisition unit. Said common acquisition apparatus may be for example a C-arm X-ray system. Using the latter it is possible, by rotation around the body, not only to generate a 3D dataset but also to acquire one or more 2D projection images sequentially in time. The control and computing unit is configured to control the generation and subsequent processing of the acquired images. In this way the method may be performed by the device.

DETAILED DESCRIPTION

Figure 1:
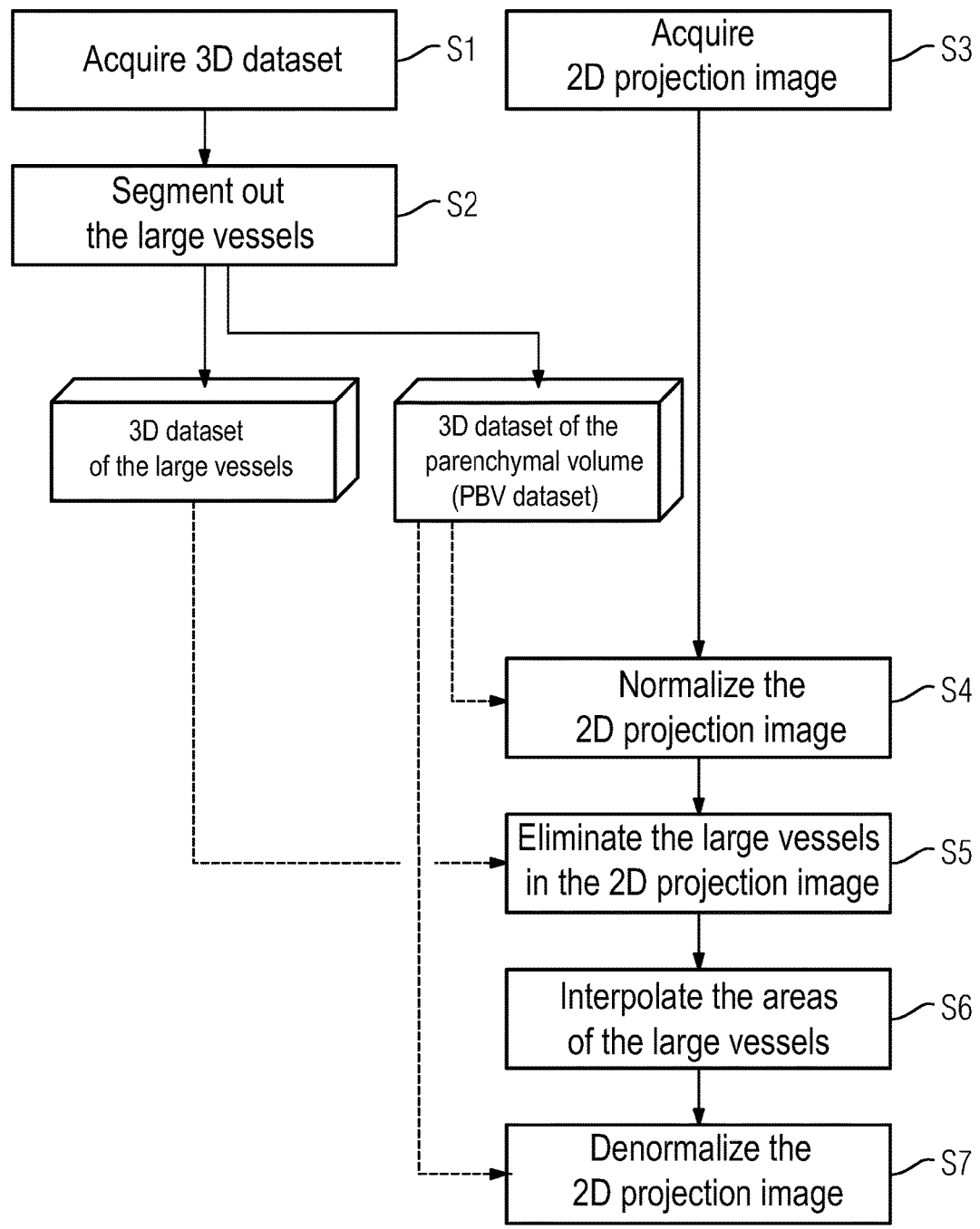
FIG. 1 depicts a flowchart intended to illustrate acts of an exemplary embodiment of the method.

The individual method acts according to an exemplary embodiment are described below with reference to FIG. 1. In a first act S1, a 3D dataset of the vascular system is acquired by an angiography system, for example a C-arm device. The dataset may be acquired on the basis of a difference calculation between a fill image in which the vascular system is filled with contrast agent statically, e.g., uniformly or in a "steady state", and a reference image that is free of contrast agent. The result of the 3D acquisition is a three-dimensional, static visualization of the vascular system. The acquisition contains not only the large afferent and efferent vessels (e.g., arteries, veins) but also the vessels of the parenchyma (in particular, the so-called microcirculation). All of the vessels may be segmented if necessary.

In a second act S2, those vessels whose size exceeds a predetermined limit value are segmented. This may be carried out on the basis of known segmentation methods, for example, by threshold-value-based segmentation. Alternatively, however, a manual segmentation on the basis of a 3D visualization of the dataset is also deserving of consideration, for example. The result of the segmentation is a first modified 3D dataset (e.g., segmented dataset) containing only the smaller vessels of interest (in particular, the vessels of the parenchyma). In addition, a second modified 3D dataset is generated that exclusively contains the large vessels (e.g., arteries, veins) that have been segmented out.

Acts S1 and S2 may be performed at an arbitrary point in time, independently of the following acts and/or independently of a perfusion measurement.

In a further act S3, at least one 2D projection image of the body region of interest is acquired, in particular, by digital subtraction angiography. The acquisition may be performed dynamically by obtaining a plurality of projection images sequentially as a time series shortly after injection of a contrast agent bolus in order to visualize the perfusion of the vascular system dynamically (e.g., with time information). The subsequent acts may be performed on the basis of the individual images of the acquisition series or on the basis of a parametric projection image which combines the individual images of the acquisition series and visualizes them in a common image.

In act S4, the 2D projection image is normalized on the basis of the 3D dataset of the parenchymal volume (e.g., first modified 3D dataset, PBV dataset). In this process, the 2D projection image is divided pixel by pixel by a forward projection of the 3D dataset of the parenchymal volume. The forward projection of the 3D dataset is performed in this case along the same projection direction as the 2D projection image. Toward that end a registration of the forward projection with the 2D projection image may be carried out first.

In act S5, those vessels in the 2D projection image whose size exceeds a predetermined limit value are marked or eliminated. This is accomplished, e.g., on the basis of the segmented large vessels of the 3D dataset (e.g., second modified 3D dataset). By a forward projection of the second modified 3D dataset, which exclusively contains the segmented large vessels, the corresponding large vessels are identified in the 2D projection image and may be classified as such.

In act S6, the regions of the large vessels in the 2D projection image are filled with artificial data, in particular by interpolation, e.g., non-linear interpolation. As a result of the interpolation the anatomical information of the areas hidden by the large vessels is initially lost.

In order to reintroduce at least some of said information into the image, the 2D projection image is denormalized on the basis of the 3D dataset of the parenchymal volume (e.g., first modified 3D dataset) in act S7. Toward that end, the 2D projection image is multiplied pixel by pixel by a forward projection of the 3D dataset of the parenchymal volume.

Act S3 may include the acquisition of a time series of 2D projection images in order to visualize the perfusion of the vascular system. Acts S4 to S7 are performed for each point in time of the time series, only the regions of the vascular system filled at the respective point in time being taken into account in each case in the 3D dataset.

In a further act, the post-processed individual projections may then be assembled to provide a new time-to-peak (TTP) calculation and visualization. The new visualization suppresses the large vessels.

By a time-dependent denormalization of projection values, the embodiments therefore achieve an improved representation of TTP maps, which no longer contain the large and interfering vessels. A three-dimensional dataset of the parenchymal blood volume (3D PBV dataset) may be used for this purpose. This may be acquired independently in time of the acquisition of the 2D projection (DSA acquisition or DSA series) and used on the basis of the 3D information for denormalizing a 2D DSA acquired from an arbitrary angle. A 3D dataset, once present, may therefore be used subsequently for denormalizing a plurality of 2D DSA acquisitions in order to improve their visualization.

Figure 2:
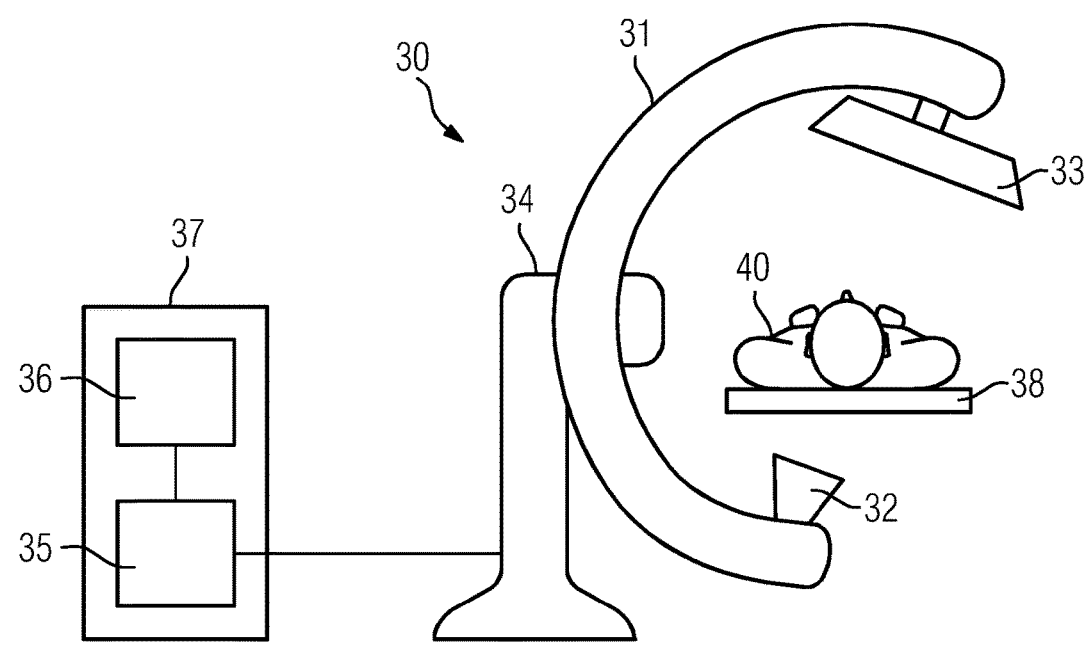
FIG. 2 depicts an embodiment of a device for performing the method.

FIG. 2 depicts a device by which the method may be performed and which itself may be embodied or configured. The device includes an acquisition apparatus 30, specifically an X-ray machine, in particular, a C-arm system. The acquisition apparatus 30 includes an X-ray source 32 and an X-ray detector 33, which are attached to the arms of a C-arm 31 that may be rotated around a patient couch 38. The X-ray detector 33 may be a digital detector that is capable of generating digital X-ray images of a patient 40 positioned on the patient couch 38. The C-arm is movably mounted on a pedestal 34.

The movements of the C-arm and the acquisition of X-ray images are controlled by a control and computing unit 35. Furthermore, the digital X-ray images acquired by the X-ray detector 33 may be transmitted to the control and computing unit 35 and processed there. The control and computing unit 35 includes a data medium or program memory 36, for example, an internal hard disk on which is stored a program code of a computer program for controlling the acquisition apparatus 30 and for processing the data obtained. The control and computing unit 35 and the program memory 36 may be part of a computer 37 that is, for example, a PC, a workstation, or a console for the acquisition apparatus 30. In addition, a screen for displaying X-ray images, as well as input devices such as keyboard and/or mouse, may also be present.

The acquisition apparatus 30 is configured for the purpose of acquiring a 3D dataset of the body region of interest, in particular, of the brain of a patient, based on acquisition of a plurality of two-dimensional projection images from different directions. In addition, the acquisition apparatus 30 is provided for the purpose of acquiring a time series of 2D projection images from a predetermined direction. The acquired series images (DSA series) may be assembled into a parametric visualization (iFlow image), which operation may be performed in the control and computing unit 35. Alternatively, however, different and/or other acquisition devices may also be provided for the acquisition of the static 3D dataset and of the 2D projection image containing the time information.

Although the invention has been illustrated and described in greater detail on the basis of an exemplary embodiment, the invention is not limited by the disclosed examples and other variations may be derived herefrom by the person skilled in the art without leaving the scope of protection of the invention.

The above-described method may be implemented via a computer program product including one or more readable storage media having stored thereon instructions executable by one or more processors of the computing system. Execution of the instructions causes the computing system to perform operations corresponding with the acts of the method described above.

The instructions for implementing processes or methods described herein may be provided on non-transitory computer-readable storage media or memories, such as a cache, buffer, RAM, FLASH, removable media, hard drive, or other computer readable storage media. A processor performs or executes the instructions to train and/or apply a trained model for controlling a system. Computer readable storage media include various types of volatile and non-volatile storage media. The functions, acts, or tasks illustrated in the figures or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Likewise, processing strategies may include multiprocessing, multitasking, parallel processing and the like.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating at least one two-dimensional (2D) projection image of a vascular system of a body region of interest, the method comprising:
    acquiring a three-dimensional (3D) angiographic image of the body region of interest including a plurality of vessels;
    acquiring at least one 2D projection image of the body region of interest including a plurality of vessel projections, wherein the at least one 2D projection image is generated by digital subtraction angiography (DSA);
    generating a modified 3D angiographic image by eliminating vessels within the plurality of vessels individually having a vessel size that exceeds a first predetermined limit value;
    normalizing the 2D projection image using projection data obtained from the modified 3D angiographic image;
    eliminating vessel projections within the plurality of vessel projections in the normalized 2D projection image individually having a vessel projection size that exceeds a second predetermined limit value;
    interpolating areas of the normalized 2D projection image in which the vessel projections have been eliminated, wherein the eliminated vessel projections and a corresponding area containing the eliminated vessel projections are filled with artifical data;
    denormalizing the normalized and interpolated 2D projection image using projection data of the modified 3D angiographic image such that parenchymal vessels included within the corresponding area of the eliminated vessel projections are reintroduced; and
    displaying, by a display apparatus, the denormalized 2D projection image.

2. The method as claimed in claim 1, wherein the vessels within the plurality of vessels of the 3D angiographic image whose size exceeds the first predetermined limit value are projected into the 2D projection image, and
    wherein the elimination of the vessel projections within the plurality of vessel projections in the normalized 2D projection image whose size exceeds the second predetermined limit value is carried out based on the plurality of vessels of the 3D angiographic image.

3. The method as claimed in claim 2, wherein the 3D angiographic image is generated by computed tomography (CT), magnetic resonance tomography (MRT), or C-arm-based imaging.

4. The method as claimed in claim 1, wherein the acquiring of the 3D angiographic image is performed based on a subtraction.

5. The method as claimed in claim 4, further comprising:
    performing a segmentation of at least the plurality of vessels in the 3D angiographic image following the acquisition of the 3D angiographic image.

6. The method as claimed in claim 1, wherein the 3D angiographic image is generated by computed tomography (CT), magnetic resonance tomography (MRT), or C-arm-based imaging.

7. The method as claimed in claim 1, wherein the at least one 2D projection image comprises a time series of 2D projection images.

8. The method as claimed in claim 7, further comprising:
    generating a final 2D projection image from the time series of 2D projection images, the final 2D projection image comprising time information about an inflow of contrast agent into the vascular system.

9. The method as claimed in claim 8, wherein an associated modified 3D angiographic image is generated for each image of the time series of projection images, wherein regions of the vascular system that are not filled with the inflow of contrast agent in the respective 2D projection image are eliminated in the 3D angiographic image, and
    wherein the normalizing, the denormalizing, or both the normalizing and the denormalizing are/is performed for each image of the time series of projection images based on the associated modified 3D angiographic image in each case.

10. The method as claimed in claim 7, wherein an associated modified 3D angiographic image is generated for each image of the time series of projection images, wherein regions of the vascular system that are not filled in the respective 2D projection image are eliminated in the 3D angiographic image, and
    wherein the normalizing, the denormalizing, or both the normalizing and the denormalizing are/is performed for each image of the time series of projection images based on the associated modified 3D angiographic image in each case.

11. The method as claimed in claim 1, further comprising:
    performing a segmentation of at least the pluralty of vessels in the 3D angiographic image following the acquisition of the 3D angiographic image.

12. The method as claimed in claim 1, wherein the normalizing is performed pixel by pixel, the denormalizing is performed pixel by pixel, or both the normalizing and the denormalizing are performed pixel by pixel.

13. The method as claimed in claim 1, further comprising:
    displaying, by the display apparatus, the modified 3D angiographic image.

14. The method as claimed in claim 1, wherein the generating of the modified 3D angiographic image comprises eliminating afferent vessels and efferent vessels.

15. A computing device comprising:
    at least one processor; and
    at least one non-transitory computer readable medium including computer program code for one or more programs; the at least one non-transitory computer readable medium and the computer program code configured to, with the at least one processor, cause the computing device to at least perform:
    acquire a three-dimensional (3D) angiographic image of the body region of interest including a plurality of vessels;
    acquire at least one 2D projection image of the body region of interest including a plurality of vessel projections, wherein the at least one 2D projection image is generated by digital subtraction angiography (DSA);
    generate a modified 3D angiographic image by eliminating vessels within the plurality of vessels individually having a vessel size that exceeds a first predetermined limit value;
    normalize the 2D projection image using projection data obtained from the modified 3D angiographic image;
    eliminate vessel projections within the plurality of vessel projections in the normalized 2D projection image individually having a vessel projection size that exceeds a second predetermined limit value;

interpolate areas of the normalized 2D projection image in which the vessel projections have been eliminated, wherein the eliminated vessel projections and a corresponding area containing the eliminated vessel projections are filled with artifical data;

denormalize the normalized and interpolated 2D projection image using projection data of the modified 3D angiographic image such that parenchymal vessels included within the corresponding area of the eliminated vessel projections are reintroduced; and display the denormalized 2D projection image.

16. A device for generating at least one 2D projection image of a vascular system of a body region of interest, the device comprising:

a first acquisition apparatus for acquiring a 3D angiographic image of the body region of interest;

a second acquisition apparatus for acquiring at least one 2D projection image of the body region of interest, wherein the at least one 2D projection image is generated by digital subtraction angiography (DSA); and a computing device having at least one processor, the computing device configured to:

acquire the three-dimensional (3D) angiographic image of the body region of interest including a plurality of vessels;

acquire the at least one 2D projection image of the body region of interest including a plurality of vessel projections;

generate a modified 3D angiographic image by eliminating vessels within the plurality of vessels individually having a vessel size that exceeds a first predetermined limit value;

normalize the 2D projection image using projection data obtained from the modified 3D angiographic image;

eliminate vessel projections within the plurality of vessel projections in the normalized 2D projection image individually having a vessel projection size that exceeds a second predetermined limit value;

interpolate areas of the normalized 2D projection image in which the vessel projections have been eliminated, wherein the eliminated vessel projections and a corresponding area containing the eliminated vessel projections are filled with artifical data;

denormalize the normalized and interpolated 2D projection image using projection data of the modified 3D angiographic image such that parenchymal vessels included within the corresponding area of the eliminated vessel projections are reintroduced; and display the denormalized 2D projection image.

* * * * *